(12) United States Patent
Miyazaki et al.

(10) Patent No.: US 9,448,163 B2
(45) Date of Patent: Sep. 20, 2016

(54) METHOD FOR DETECTING RARE CELL ON OBSERVATION REGION

(75) Inventors: Koji Miyazaki, Tokyo (JP); Jungo Araki, Tokyo (JP); Tsuneko Chiyoda, Tokyo (JP)

(73) Assignee: KONICA MINOLTA HOLDINGS, INC., Tokyo (JP)

( * ) Notice: Subject to any disclaimer, the term of this patent is extended or adjusted under 35 U.S.C. 154(b) by 1048 days.

(21) Appl. No.: 13/581,493

(22) PCT Filed: Feb. 25, 2011

(86) PCT No.: PCT/JP2011/054292
§ 371 (c)(1),
(2), (4) Date: Aug. 28, 2012

(87) PCT Pub. No.: WO2011/108454
PCT Pub. Date: Sep. 9, 2011

(65) Prior Publication Data
US 2012/0322046 A1 Dec. 20, 2012

(30) Foreign Application Priority Data
Mar. 5, 2010 (JP) .................... 2010-049014

(51) Int. Cl.
*G01N 15/14* (2006.01)
*G01N 21/27* (2006.01)
*G01N 33/49* (2006.01)

(52) U.S. Cl.
CPC .......... *G01N 21/27* (2013.01); *G01N 15/1463* (2013.01); *G01N 33/491* (2013.01)

(58) Field of Classification Search
None
See application file for complete search history.

(56) References Cited

U.S. PATENT DOCUMENTS

| | | | |
|---|---|---|---|
| 2004/0142463 A1* | 7/2004 | Walker | A61M 1/36 435/325 |
| 2008/0206757 A1* | 8/2008 | Lin | G01N 33/5094 435/6.14 |
| 2011/0104718 A1* | 5/2011 | Rao | G01N 33/54326 435/7.23 |
| 2012/0276555 A1* | 11/2012 | Kuhn | G01N 33/5076 435/7.23 |
| 2015/0079677 A1* | 3/2015 | Yamanishi | C12Q 1/6881 435/372 |
| 2015/0276564 A1* | 10/2015 | Araki | B01L 3/502761 435/30 |

FOREIGN PATENT DOCUMENTS

| | | |
|---|---|---|
| JP | 60-38653 | 2/1985 |
| JP | 3-94159 | 4/1991 |
| JP | 6-500403 | 1/1994 |
| JP | 2002-503814 | 2/2002 |
| JP | 2002-514762 | 5/2002 |
| JP | 2004-138614 | 5/2004 |
| JP | 2004-522937 | 7/2004 |
| JP | 2006-087424 | 4/2006 |
| JP | 2006-133001 | 5/2006 |
| JP | 2007-502419 | 2/2007 |
| JP | 2009-027942 | 2/2009 |
| JP | 2009-204407 | 9/2009 |
| WO | 0049391 A1 | 8/2000 |
| WO | 2008085777 A2 | 7/2008 |

OTHER PUBLICATIONS

Kojima T. et al. A Simple Biological Imaging System for Detecting Viable Human Circulating Tumor Cells. J Clinical Investigation 119(10)3172-3181, Oct. 2009.*
NUNC(TM) LiveCell Array(TM) protocol guide from Biotechniques, 2007.*
Office Action dated Apr. 21, 2015 from the corresponding Japanese Patent Application No. 2014-092970.
English translation of the Office Action dated Apr. 21, 2015 from the corresponding Japanese Patent Application No. 2014-092970.
Katsumi Kojima Part 1 "Taking peripheral blood and specimen preparation" of Chapter 2 "Preparation and preservation of specimen", Modern Medical Laboratory, 2009, vol. 37, No. 10, p. 1065-1067.
Kojima Toru et al, A simple biological imaging system for detecting viable human circulating tumor cells, J Clin Investig, 2009, vol. 119, No. 10, p. 3172-3181, Measurement of viable CTCs with OBP-401 in the blood, Figure 2.
Katsumi Higashi, "2 Hyohon no Sakusei to Hozon 1-Massho Ketsueki no Saishu to Hyohon Sakusei", Modern Medical Laboratory, 2009, vol. 37, No. 10, pp. 1065 to 1067, 2 Ketsueki Tomatsu Hyohon Sakusei.
European Search Report dated Feb. 26, 2016: Application No./ Patent No. 11750564.4-1553 / 2543999 PCT/JP2011054292; Applicant: Konica Minolta Holdings, Inc.; total of 12 pages.
Tokimitsu Y et al: "Single Lymphocyte Analysis with a Microwell Array Chip", Cytometry. Part A, John Wiley & Sons, Inc, US, vol. 71, No. 12, Dec. 1, 2007, pp. 1003-1010, XP002561038, ISSN: 1552-4930, DOI: 10.1002/CYT0.A.20478 [retrieved on Oct. 30, 2007] paragraph [materialsandmethods].
Kenneth L. Roach et al: "High Throughput Single Cell Bioinformatics", Biotechnology Progress., Jan. 1, 2009, pp. NA-NA, XP055250872, US; ISSN: 8756-7938, DOI: 10.1002/btpr.289; paragraph [materialsandmethods]; figure 1.
Sara Lindstrom et al: "High-Density Microwell Chip for Culture and Analysis of Stem Cells", PLOS ONE, vol. 4, No. 9, Jan. 1, 2009, pp. e6997-e6997, XP055022128, ISSN: 1932-6203, DOI: 10.1371/ journal.pone.0006997; figures 1,2.

* cited by examiner

*Primary Examiner* — Ralph Gitomer
(74) *Attorney, Agent, or Firm* — Lucas & Mercanti, LLP

(57) ABSTRACT

The detection of rare cells can be achieved with high efficiency, without deteriorating the sensitivity of the detection. A detection method which enables the above-mentioned detection comprises: a first step of carrying out a pretreatment for removing erythrocytes from blood to prepare a cell suspension containing leukocytes and rare cells; a second step of providing all of the cells contained in the cell suspension produced in the first step onto an observation area having multiple holes formed thereon; a third step of taking an optical image of the cells that have been provided on the observation area; and a forth step of detecting the rare cells from the image obtained by the image taking in the third step.

2 Claims, 7 Drawing Sheets

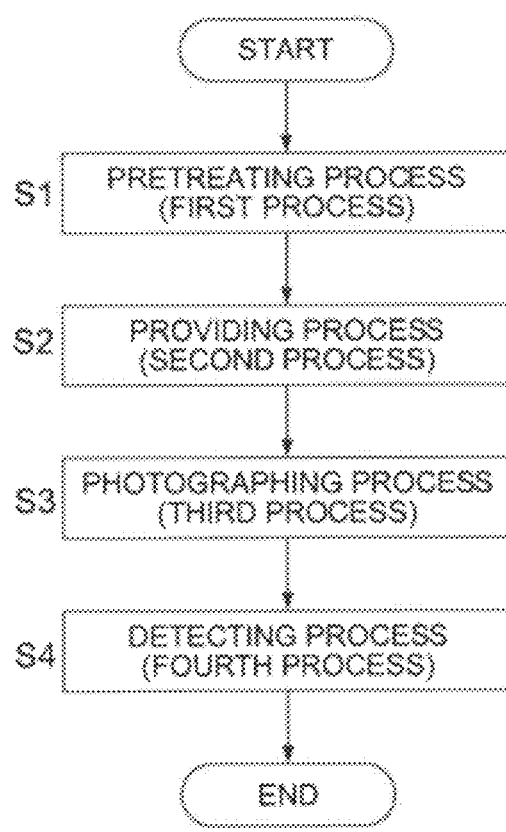

4a

4b wbc

METHOD FOR DETECTING RARE CELL ON OBSERVATION REGION

CROSS REFERENCE TO RELATED APPLICATION

This Application is a 371 of PCT/JP2011/054292 filed on Feb. 25, 2011 which, in turn, claimed the priority of Japanese Patent Application No. 2010-049014 filed on Mar. 5, 2010, the entire content of which is incorporated by reference herein.

TECHNICAL FIELD

This application relates to a detection method for detecting cells in blood, in particular, circulating tumor cells (CTC: circulating tumor cell), and to a cell detecting system.

BACKGROUND ART

Tumor cells exist in the blood of a cancer patient.

The detection of existence or non-existence of tumor cells in the circulating blood enables to judge whether to suffer from cancer, or to judge the effect of treatment to a cancer patient.

The concentration of tumor cells is very low such that only several tumor cells exist with such a low concentration among $10^7$ to $10^8$ cells. For example, the number of tumor cells contained in the sample of 10 ml of blood is as small as 4 to 5.

According to she method disclosed by Patent Document 1, rare cells are separated from the blood by use of magnetic panicles coupled with biologically-specific ligand which reacts specifically with rare cells (rare cell), such as circulating tumor cells; the separated rare cells are labeled, and the labeled rare cells are observed, thereby detecting the existence of rare cells and the number of rare cells.

According to the device disclosed by Patent Document 2, a blood sample treated with a fluorescent substance is pasted on a transparent slide glass, the transparent slide glass is scanned with a radiation beam so as to emit light, the light is converted into optical signals, and the optical signals are processed, thereby detecting rare substances.

RELATED ART DOCUMENT

Patent Documents

Patent documents 1: Japanese Unexamined Patent Publication No. 2002-503814 Official Report
Patent documents 2: Japanese Unexamined Patent Publication No. 2004-138614 Official Report

OUTLINE OF THE INVENTION

Problems to be Solved by the Invention

In Patent document 1, since the rare cells are separated from the blood by use of the magnetic particles, in this process, all the rare cells becoming essentially as a target cannot be always separated, and there is a possibility that capture failure may occur depending on the nature of cells.

Further, in Patent Document 2, cells labeled with a fluorescent substance are coated on to a transparent slide glass to form smear specimen, and then the smear specimen is observed.

In Patent Documents 1 and 2, in the process that cells to be made to the target of the observation are extracted or rare cells are detected with restriction, there is a possibility that capture failure may occur, which results in that detection sensitivity may fall.

In order to prevent the capture failure from occurring, it may be better to observe all the rare cells and leukocytes cells which become as a target. In the case of observation of ah the cells, it is required to provide the target cells on a observation region so as not to overlap with each other. However, if the cells are simply spread, the size of the detection device becomes larger, which is not a real way.

In view of die above problems, an object of the present invention is to provide a cell detecting method and a cell detecting system which can detect rare cells efficiently without lowering detection sensitivity.

Means for Solving the Problems

The above-mentioned purpose can be attained by the invention described below.

1. A cell detecting method for detecting rare cells in a blood sample,
a first process of performing pretreatment to remove red blood cells from a blood sample so as to obtain a cell suspension liquid containing leukocyte cells and rare cells;
a second process of providing (spreading or developing) all the cells contained in the cell suspension liquid obtained at the first process onto an observation region provided wife a plurality of holes;
a third process of photographing optically the cells provided on the observation region; and
a fourth process of detecting rare cells from, an image acquired by the photographing in the third process.

2. The cell detecting method described in Item 1, characterized in that the plurality of holes disposed on the observation region are formed by wells arranged with a predetermined pitch, and in the second process, the cells are made to deposit in the wells so that all the cells contained in the cell suspension liquid are provided.

3. The cell detecting method described in Item 2, characterized in that each of the wells has an upper hole diameter less than two times the maximum diameter of the cells provided on the observation region.

4. The cell detecting method described in Item 2, characterized in that each of the wells has an upper hole diameter equal to or larger than two times the maximum diameter of the cells provided on the observation region.

5. The cell detecting method described in Item 1, characterized in that the plurality of holes disposed on the observation region are formed by a filter having a plurality of through holes which are disposed with a predetermined pore density and each of which has a diameter smaller than the maximum diameter of the cells contained in the cell suspension liquid, and in the second process, the cell suspension liquid is made to pass thorough the filter so that all the cells contained in the cell suspension liquid are provided on the filter.

6. A cell detecting method for detecting rare cells in a blood sample,
a first process of performing pretreatment to remove red blood cells from a blood sample so as to obtain a cell suspension liquid containing leukocyte cells and rare cells;
a second process of spreading all the cells contained in the cell suspension liquid obtained at the first process into a thin layer with a thickness smaller than two times the maximum diameter of the cells so that all die cells are provided on the observation, region;

a third process of photographing optically the cells provided on the observation region; and a fourth process of detecting rare cells from an image acquired by the photographing in the third process.

7. The cell detecting method described in Item 6, characterized in that in the second process, the cells contained in the cell suspension liquid are provided on the observation region by a spin coating method.

8. The cell detecting method described, in Item 6, characterized in that in the second process, the cells contained in the cell suspension liquid are provided on the observation region by a bar coating method.

9. A cell detecting system comprises:

an observation unit which is provided with a plurality of holes and on which all cells contained in a cell suspension liquid obtained via pretreatment to remove red blood cells from a blood sample are provided;

a photographing section to photograph optically all the cells provided on the observation unit; and an analysing section to detect rare cells from an image acquired by the photographing section, wherein the plurality of holes disposed on the observation region are formed by wells arranged with a predetermined pitch, and the cells are made to deposit in the wells so that all the cells contained in the cell suspension liquid are provided.

10. The cell detecting system described in Item 9, characterized in that each of the wells has an upper hole diameter less than two times the maximum diameter of the cells contained in the cell suspension liquid.

11. The cell detecting system described in Item 9, characterized in that each of the wells has an upper hole diameter equal to or larger than two times the maximum diameter of the cells contained in the cell suspension liquid.

12. A cell detecting system comprises:

an observation unit which is provided with a plurality of holes and on which all cells contained in a cell suspension liquid obtained via pretreatment to remove red blood cells from a blood sample are provided;

a photographing section to photograph optically all the cells provided on the observation unit; and an analyzing section to detect rare cells from an image acquired by the photographing section, wherein the plurality of holes disposed on the observation region are formed by a filter having a plurality of through holes which are disposed with a predetermined pore density and each of which has a diameter smaller than the maximum diameter of the cells contained in the cell suspension liquid, and the cell suspension liquid is made to pass thorough the filter so that all the cells contained in the cell suspension liquid are provided on the filter Effect of Invention According to the present invention, with a process of providing all cells contained in a cell suspension liquid obtained via pretreatment to remove red blood cells from a blood sample onto an observation region provided with a plurality of holes; or a process of spreading into a thin layer with a thickness smaller than two times the maximum diameter of the cells so that the cells are provided on the observation region, all the cells can be provided on a narrow region by suppressing overlapping between cells, whereby it becomes possible to detect rare cells without deteriorating the detection sensitivity.

BRIEF DESCRIPTION OF TEE DRAWINGS

FIG. 2 is a flaw diagram for explaining a detection method of detecting rare cells according to a present embodiment.

EMBODIMENT FOR CARRYING OUT THE INVENTION

The present invention will be explained based on embodiments. However, the present invention is not limited to the embodiments.

Figure 1:
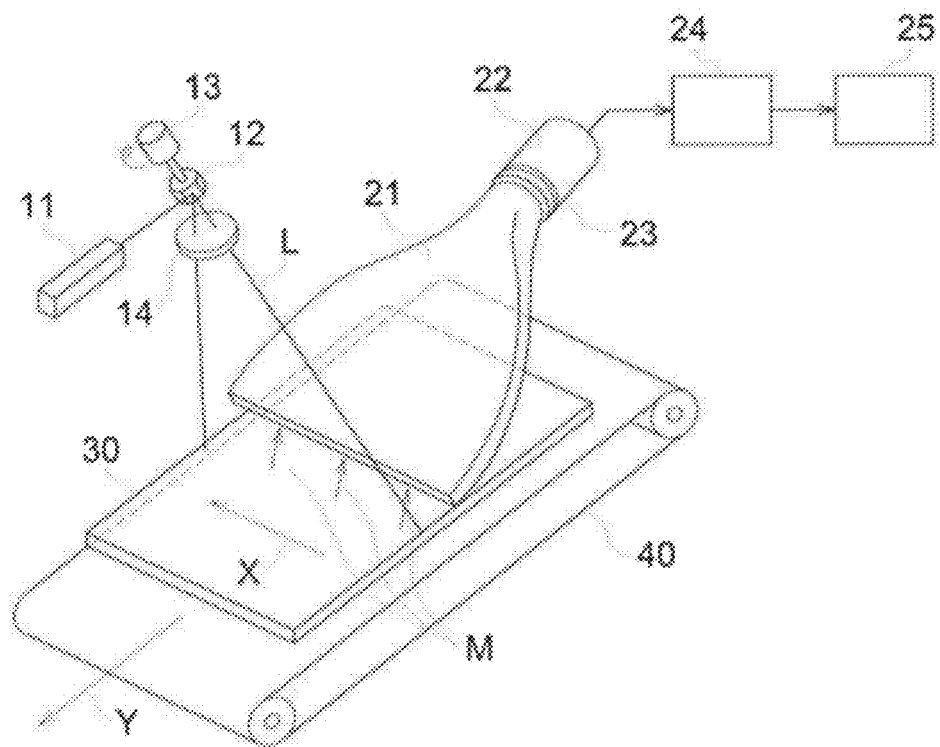
FIG. 1 is a diagram showing an outline constitution of a cell detection system according to a present embodiment.
Figure 3A:
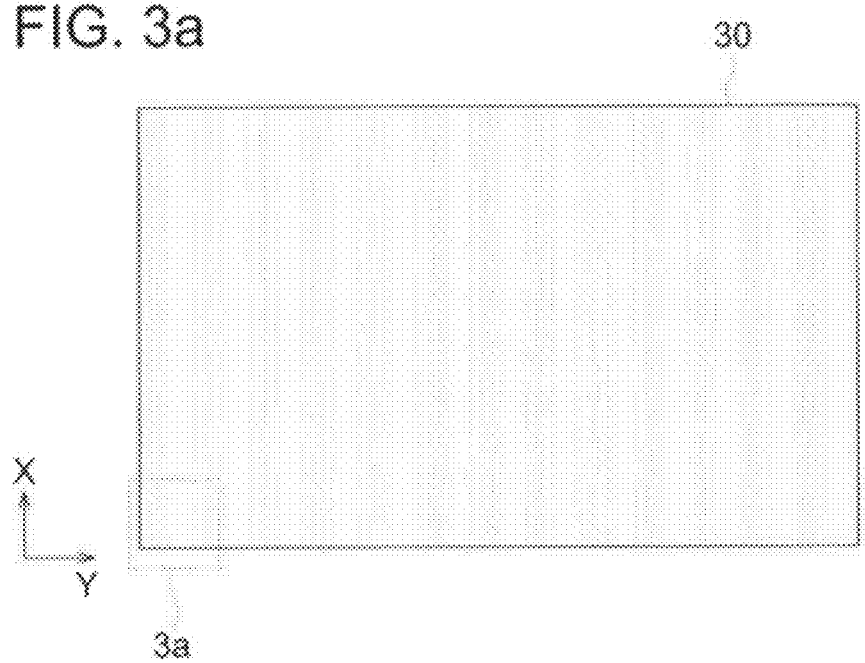
FIG. 3 shows a first example of an observation unit 30 employing a MWC method as one of the providing methods.
Figure 3B:
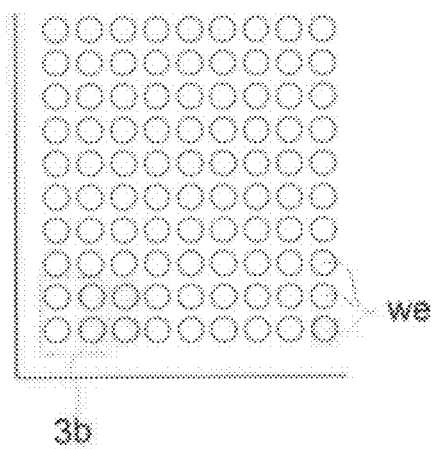
Figure 3C:
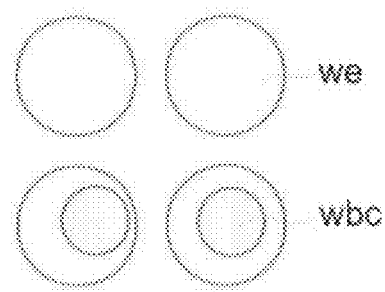
Figure 3D:
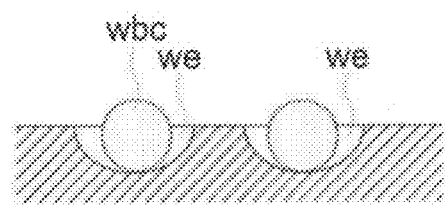

FIG. 1 is an illustration showing a constitution of an outline of a cell detection system according to one embodiment.

In the cell detection system shown in the illustration, an observation unit 30 is disposed on an endless belt 40 configured to be rotated by a not-shown motor. Above the observation unit 30, a light source 11, a rotatable polygon mirror 12, a motor 13, and a scanning optical system 14 are disposed. The light source 11 is configured to emit an irradiation light beam (laser beam) L with a predetermined wavelength. The rotatable polygon mirror 12 is configured to reflect and deflect the irradiation light beam L. The motor 13 is configured to rotate the rotatable polygon mirror 12. The scanning optical system 14 is configured to make the irradiation light beam L, which is reflected and deflected by the rotatable polygon mirror 12, to converge onto the observation unit 30, and to further make the irradiation tight beam L to scan at an equal speed on the observation unit 30.

Just above an upper portion of the observation unit 30 where the irradiation light beam L scans, an optical guide 21 is disposed in close proximity to the upper portion so as to collect reflected light rays M from above them when the reflected light rays M are generated from die upper portion of the observation unit 30 irradiated with the irradiation light beam L. To the optical guide 21, a light receiving section 22 is connected. Moreover, between the light receiving section 22 and the optical guide 21, an optical filter 23 is disposed so as to cut off light wavelength components other than the wavelength of the irradiation light beam L in order to prevent unnecessary light components other than the reflected tight rays M from entering the light receiving section 22.

To the light receiving section 22, a photographing section 24 is connected. The photographing section 24 is configured to process digital signals output from the light receiving section 22, converts them to digital image data, and outputs the digital image data to an analyzing section 25 disposed at a subsequent stage.

Hereafter, an outline of the actions of the cell detection system shown in the illustration of operation will be explained briefly.

The observation unit 30 is shaped in a plate which is made of material such as glass and has a smooth surface. The surface is constituted to allow cells in the blood subjected to pretreatment mentioned later to be provided thereon. The observation unit 30 is configured to be set at a predetermined position on an endless belt 40 and to be conveyed (sub-scan) in the arrowed direction Y by the movement of the endless belt 40.

On the other hand, an irradiation light beam (laser light beam) L emitted from the light source 11 is reflected and deflected by the rotatable polygon mirror 12 which is rotated at a high speed by the motor 13. This reflected-deflected irradiation light beam L is made to converge on the surface of the observation unit 30 by the scanning optical system 14 and to scan (main-scan) at an equal speed in the arrowed direction X on the surface of the observation unit 30. With the main-scan of the irradiation light beam L in the arrowed direction X and the sub-scan of the observation unit 30 in the arrowed direction Y, the irradiation light beam L is irradiated over to the whole surface of the observation unit 30. The whole surface of fire observation unit 30 is configured to serve as an observation region.

The reflected light rays M emitted sequentially from the upper portion of the observation unit 30 irradiated with the irradiation light beam L are led to the light receiving section 22 by the optical guide 21 disposed in close proximity to the upper portion of the observation unit 30.

The light receiving section 22 detects the entered reflected light rays M, converts the detected reflected light rays M respectively into image signals corresponding to the light quantity of them, and outputs the image signals to the photographing section 24. In the photographing section 24, the image signals are sampled with a predetermined sampling interval in synchronization with the scan of the irradiation light beam L and converted into digital image data for each pixel by quantization. The photographed images are sent to the analyzing section 25. As mentioned later, the analyzing section 25 is configured to conduct extraction of cells and selection of leukocyte cells, tumor cells, and other rare cells (rare cells) from the extracted cells.

[Detection Method]

FIG. 2 is a flaw diagram for explaining the detection method, according to this embodiment, for detecting rare cells.

In a pretreating process (the first process) at Step S1, the blood sampled from an examinee is subjected to pretreatment. The pretreatment is achieved so as to remove at least red blood cells, platelets, and the like from the blood. In addition, a stabilizing agent may be put into the blood, or the blood may be diluted into a predetermined concentration. For example, the sampled blood is mixed with a stabilizing agent, and the mixture is subjected to centrifugal separation at 1500 rpm for five minutes so as to remove supernatant liquid. Thereafter, the remaining leukocyte layer (buffy coat) is used for the examination. Alternately, the blood may be added into a liquid with a middle specific gravity between leukocyte cells and red blood cells, the resulting liquid is subjected to centrifugal separation, and then the supernatant liquid containing leukocyte cells may be used for the examination. This procedure may reduce the risk to lose some leukocyte cells (and rare cells) from supernatant liquid. Hereafter, the pretreated blood is called a cell suspension liquid. In this connection, the cell suspension liquid contains at least leukocyte cells (leukocyte cells and rare cells depending on the case).

In a providing process (the second process) at Step S2, the cell suspension liquid produced at Step S1 is provided onto the observation unit 30 on which a plurality of holes are provided. With this providing process, all cells are effectively disposed in the form of almost a single layer in a narrow area on the observation unit 30. The providing method will be described later in detail.

In a photographing process (the third process) at Step S3, the cells (mainly leukocyte cells) provided on the observation unit 30 are photographed by the photographing section 24 so as to produce image data.

In a detecting process (the fourth process) at Step S4, the image data obtained at Step S3 are subjected to image processing by the analyzing section 25 so as to detect existence or nonexistence of tumor cells and other rare cells and the number of them. One example of the detecting method may be conducted in the following ways. The obtained image data are subjected, to contrast adjustment, binarization process, and edge extraction so as to detect a plurality ($10^7$ to $10^8$) of cells and to obtain shape information of them. Further, from the shape information of a cell Shape, features are extracted, and then in the case where the extracted shape features are different from those of normal leukocyte cells, the cell is judged as a rare cell. At this time, in the providing process at Step S2, the plurality of cells are efficiently disposal in the form of a single layer so as not to overlap with each other in a narrow area on the observation unit 30. Subsequently, in the detecting process at Step S4, it can be judged for all the cells whether to be a normal leukocyte cell or the other rare cell. All the cells are packed to be not likely to overlap with each other in terms of the height direction in which photographing is conducted and to be in a state near to the closest packing in terms of the planar direction, whereby all the cells are disposed efficiently in the narrow area. Accordingly, the observation unit 30 is not needed to have a large area. As a result, it is not necessary to constitute a detecting unit in a larger size.

[Other Detection Methods]

Furthermore, by performing immobilization and dyeing of cells as explained below, cells can be observed more correctly. Examples of the methods for immobilizing cells include a formalin method, a methanol method, and the like. Examples of the methods for dyeing cells include a DAPI dyeing method to dye DNA in a nuclear, a Hoechst dyeing method, and an immunostaining method which employs an antibody specifically reacting wife cell species. Examples of immunostaining include leukocyte common antigen CD45 and tumor marker CK (cytokeratin).

In the case where these immobilizing and dyeing operations are performed, these operations are performed as Step S1-2 between Step S1 and Step S2 for precipitate obtained at Step S1. Alternately, these operations are performed as Step S2-2 between Step S2 and Step S3 for cells provided at Step S2 in die observation unit 30.

[Providing (Spreading or Developing) Method]

The method for providing a cell suspension liquid onto the observation unit 30 is classified broadly into two methods, that is, (1) a method for providing an extremely small amount of a cell suspension liquid in a predetermined pitch, and (2) a method for spreading a specified amount of a cell suspension liquid in a plain direction so as to provide it into a thin layer.

(1) Examples of the method for providing in a predetermined pitch, include a MWC method and a through-hole filter method. The MWC method and the through-hole filter method will be described later in detail. Here, a pitch means a (average) distance between respective centers of neighboring objects, for example, a distance between wells mentioned later and a distance between respective centers of filter holes.

In all the methods, a cell suspension liquid is coated (disposed) in a pitch equal to or more than the size (5 to 30 μm in diameter) of a leukocyte cell (arrangement), for example, a pitch of 0 to 50 μm. Further, when the amount of taken blood is 10 ml, the number of provided cells becomes $10^7$ to $10^8$. Accordingly, the area of the observation unit 30 is needed to be 10 cm square (in the case of $10^7$ in number in 32 μm pitch) to an A-4 sheet size (in the case of $10^7$ in number in 50 μm pitch).

(2) The method for providing into a thin layer is classified broadly into two of a spin coating method and a bar coating method. Further, the ban coating method is classified into a gap coating method and a wire bar coating method.

In "the spin coating method", the observation unit 30 is fixed via vacuum suction and the like, a cell suspension liquid is dropped onto the top surface of the observation unit 30, and that a device called a spinner (Spinner) is rotated at high speed for a given time period so as to provide the dropped cell suspension liquid into a predetermined thin layer on the observation unit 30. The rotation speed of foe spinner may be determined depending to the concentration (viscosity) of a cell suspension liquid. However, a cell suspension liquid may be provided uniformly by a rotation speed of 100 to 5000 rpm.

In "the bar coating method", a bar-shaped member arranged above the top surface of the observation, unit 30 with a predetermined gap (coating gap) is slid on a cell suspension liquid dropped on the observation unit 30 (gap coating method). Alternatively, a wire bar in which a wire with a certain diameter is wound around a round bar is slid in a state of being in contact with the top surface of the observation unit 30 (wire bar method). In the above ways, a cell suspension liquid is made in a thin layer with a predetermined layer thickness on the observation unit 30. A coating gap in the gap coating method may be preferably less than several times the maximum diameter of cells contained in a cell suspension liquid. In this embodiment, the target cells are leukocytes and rare cells (especially, tumor cells), and the maximum diameter of these cells is about 20 to 100 μm. Accordingly, a coating gap may be made 50 to 300 μm being several times the maximum diameter. The diameter of a wire wound in the wire bar may be preferably 100 to several hundreds μm.

In all the methods, appropriate conditions ensures to obtain a thin layer with a thickness less than two times the maximum diameter (about 30 μm) of target leukocyte cells (a diameter of 10 to 30 μm) so that cells do nor overlap with each other on the observation unit 30.

MWC (Micro Well Chamber) Method

First Example

FIG. 3 shows the first example of an observation unit 30 which employs the MWC method as one of the providing methods. FIG. 3(a) is a top plan view of the observation unit 30, FIG. 3(b) is an enlarged view of a frame 3a in FIG. 3(a), FIG. 3(c) is an enlarged view of a frame 3b in FIG. 3(b), and FIG. 3(d) is a cross sectional view of FIG. 3(c). As shown in these figures, in the observation unit 30 of the MWC method, a lot of wells we are arranged in the form of a plane surface with an equal pitch.

In the example shown in FIG. 3, each well we is shaped in a hemispherical form. The upper hole diameter (diameter by a top surface view) of each well we is made into a large diameter than the diameter of each cell to be provided. The size of each well we is approximately equal to a size to accommodate leukocyte cells wbc (and rare cells) one by one, and is preferably less than two times the maximum diameter leukocyte cells and other cells. For example, a depth (height at the center portion) is 5 to 30 μm, aid a diameter (upper hole diameter) is 10 to 35 μm. A distance between neighboring wells we is 0 to 20. A pitch in the arrangement of them is made larger than the diameter of the well we, and is about 10 to 50 μm. Each well we is disposed over an area of 0.01 $m^2$.

By employment of the observation unit 30 of the MWC method which can dispose all cells contained in a cell suspension liquid in respective wells we by spreading or providing the cell suspension liquid onto the entire top surface of the observation unit 30 and by causing natural sedimentation and microscopic vibration in the cell suspension liquid, it becomes possible to provide all the cells so as not to overlap with each other.

Second Example

FIG. 4 shows the second example of an observation unit 30 which employs the MWC method as one of the providing methods. FIG. 4(a) is a top plan view of the observation unit 30, FIG. 4(b) is an enlarged view of a frame 4a in FIG. 4(a), FIG. 4(c) is an enlarged view of a frame 4b in FIG. 4(b), and FIG. 4(d) is a cross sectional view of FIG. 4(e). FIGS. 4(a) to 4(d) correspond respectively to FIGS. 3(a) to 3(d).

In the example shown in FIG. 4, different from the example shown in FIG. 3, each well we has a size which can accommodate a plurality of cells such as about several tens to several hundreds of cells. The size of each well we, for example, may be several hundreds μm in diameter (hole upper diameter). That is, the size of each well we is made equal to or larger than two times the maximum diameter of cells provided onto a observation region. The height (depth) of each well we at its deepest center portion is preferably equal to or less than several times the maximum diameter of cells, and more preferably equal to or less than two times. Such a flattened form the height of which is low as compared with a diameter is preferable in order to provide cells without making them to overlap with each other.

Figure 4A:
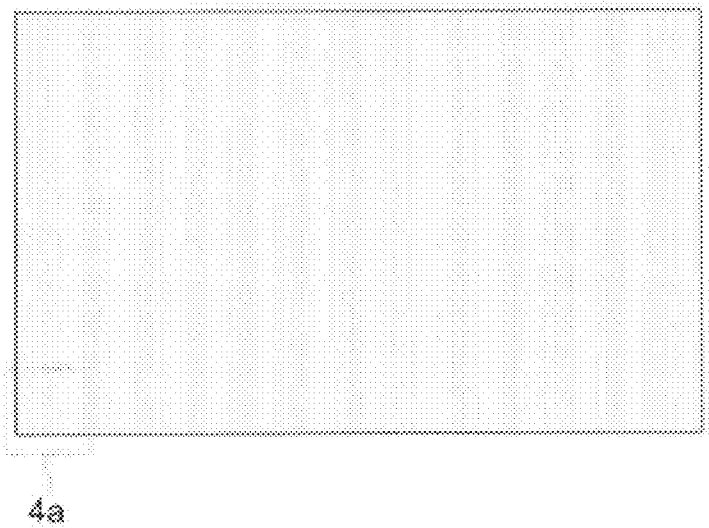
FIG. 4 shows a second example of the observation unit 30 employing a MWC method as one of the providing methods.
Figure 4B:
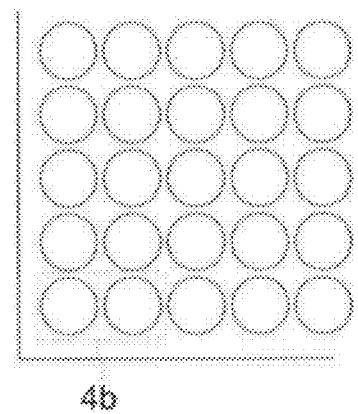
Figure 4C:
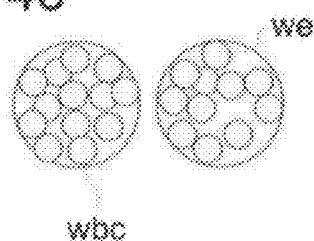
Figure 4D:

As shown in FIG. 4(c) and FIG. 4(d) in FIG. 4, about ten-odd cells (ten and several cells) are accommodated into a single well we. Since the accommodation of a plurality of cells in a single well reduces the dead space, cells can be provided in a narrow area with high density as compared with the first example shown in FIG. 3. Accordingly, the observation region can be made narrower.

In the providing of a cell suspension liquid to each well we shown in FIG. 4, it is preferable to feed the cell suspension liquid to almost the center of each well we by an ink jet method or a dispenser method. With this, when the cell suspension liquid has be fed, cells are provided and dispersed so that overlap of cells to each other can be prevented at an early stage. Examples of the ink jet method include a method of using a thermal head or a piezoelectric head. Examples of the dispenser method include a method of using a micro pipette or a micro dispenser. Either one of them is configured to coat a minute amount of liquid droplets with a prescribed interval by making jetting holes of the liquid droplets to scan at a constant speed on the surface of a material to be coated. An amount of liquid droplets to be fed to each well we is preferably several hundreds nl or less.

In the embodiment shown in FIG. 3 and FIG. 4, a circle shape by the top view is indicated as the configuration of the well we. However, the configuration should not be limited to this circle shape. For example, the configuration by the top view (cross sectional shape) may be made to a honeycomb-shaped square column, and a plurality of square columns may be arranged in a flat plane direction without providing a gap between neighboring square columns. For example, Nunc live cell array (manufactured by Nalgene Nunc International Inc.) may be employable. In this case, the diameter (in the flat plane direction) corresponds to the diameter of a circumscribing circle circumscribing to a honeycomb, and the diameter may be larger than the diameter of a cell.

[Through Hole Filter Method]

Figure 5A:
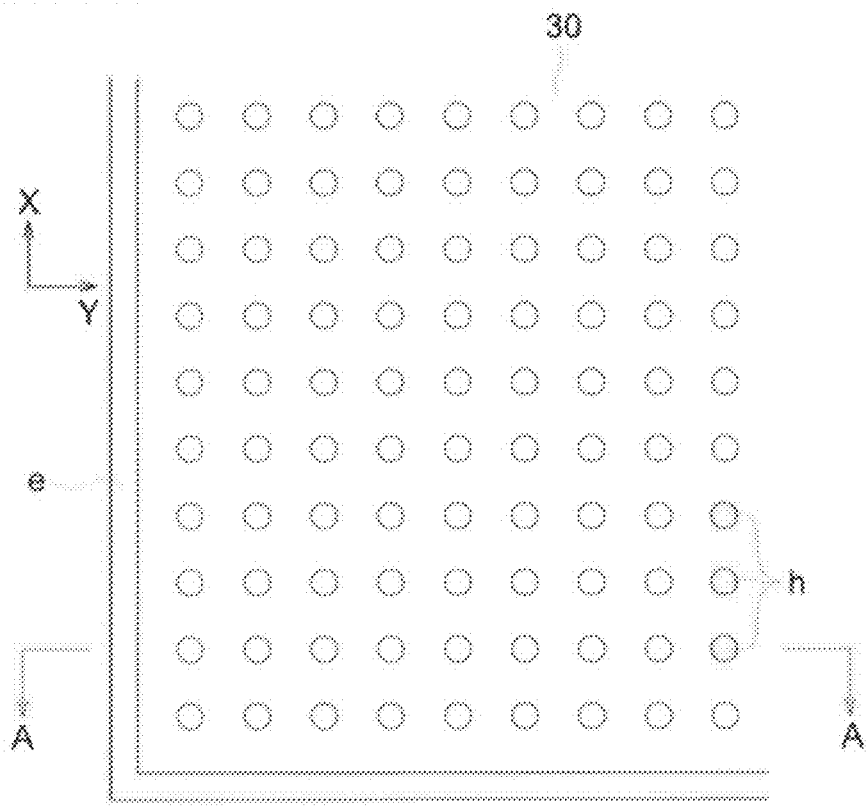
FIG. 5 shows an example of the observation unit 30 employing a through-hole filter method as one of the providing methods.
Figure 5B:
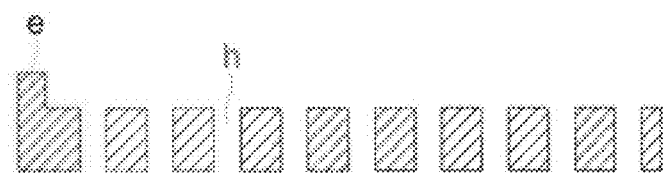
Figure 5C:
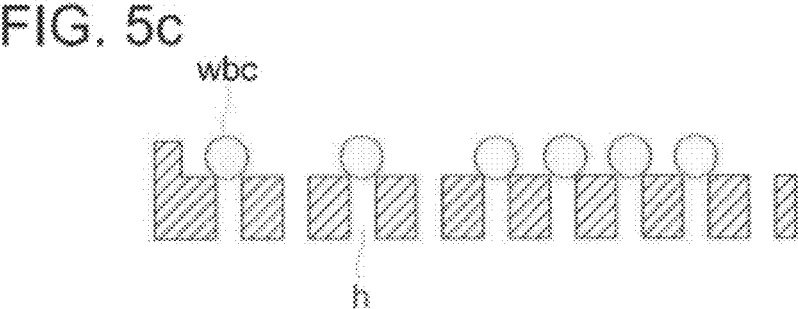

FIG. 5 shows an example of the observation unit 30 employing a through hole filter method as one of the providing method. FIG. 5(a) is a partially enlarging view of the observation unit 30, FIG. 5(b) is a A-A cross sectional view of FIG. 5(a), and FIG. 5(c) is a diagram showing a state in which leukocyte cells wbc are held by respective holes h of a filter.

In the observation unit 30 employing the through hole filter method, similarly to the embodiment shown in FIG. 3, lot of holes h are arranged over an area of 0.01 m² with a predetermined pore density. The pore density may be, for example, $1 \times 10^7$ holes/cm² to $6 \times 10^8$ holes cm². The holes h are each a through hole. The diameter of a hole h is smaller than that of each of a leukocyte cell wbc and a rare cell, and, for example, is 0.5 μm. In the embodiment shown in FIG. 5, the through-holes of the filter are arranged equally in the flat plane direction. However, the arrangement should not be limited to this arrangement. The through-holes may be arranged randomly. For example, Nuclepoer (Nuclepoer) membrane (GE Healthcare Japan Corporation, Distribution Source) may be employed.

The outer edge of the observation unit 30 is surrounded by a protruding wall portion e. In order to provide cells in a cell suspension liquid, the cell suspension liquid may be poured into the top surface of the observation unit 30. Mixtures contained in the cell suspension liquid, such as liquid, very small blood platelets and the like flow down from holes h and are discharged downward. As a result, only cells larger than the holes h remain at the upper stream of the holes h, i.e., on the top surface (on the filter) of the observation unit (FIG. 5(c)). When the liquid and the like are discharged downward, in order to advance the processing, a pressure difference may be provided between the upstream side and the downstream side of the holes h. With the employment of the observation unit 30 of such a through hole filter type, it aloes becomes possible to provide all cells on the arrangement of holes h so as not to make cells to overlap with each other.

Example

Figure 6:
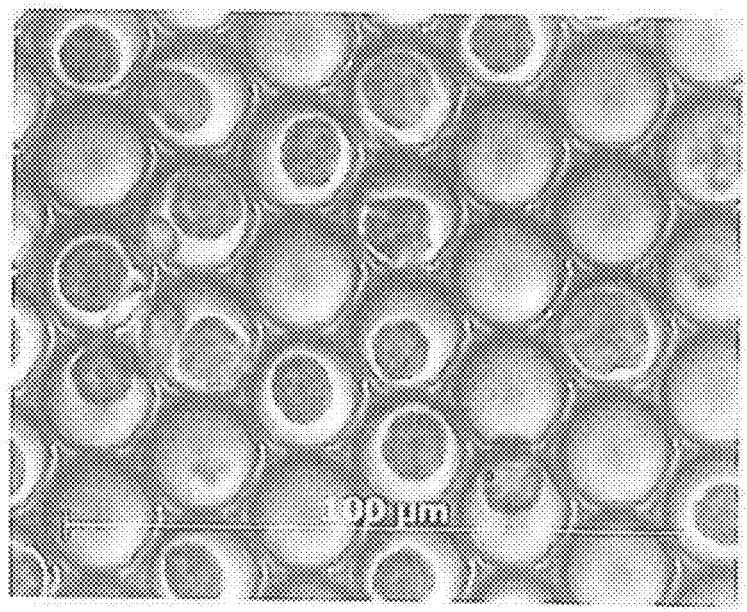
FIG. 6 shows an example of the observation unit 30 which employs a Nunc live cell array and provides one cell for each well.

Next, description will be given for an example of the observation unit 30 employing the MWC method and the through-hole filter system. FIG. 6 is a figure showing a state in which cells in a cell suspension liquid are provided (precipitated) in the observation unit 30 of the MWC system. As the observation unit 30, the Nunc live cell array is used. The cross sectional shape of each of wells we is a honeycomb shape, and the diameter (diameter of a circumscribed circle) of the wells we is 20 μm. It turns out that a single cell is provided for each of the wells we of the observation unit 30 such that the cells do not overlap with each other.

Figure 7:
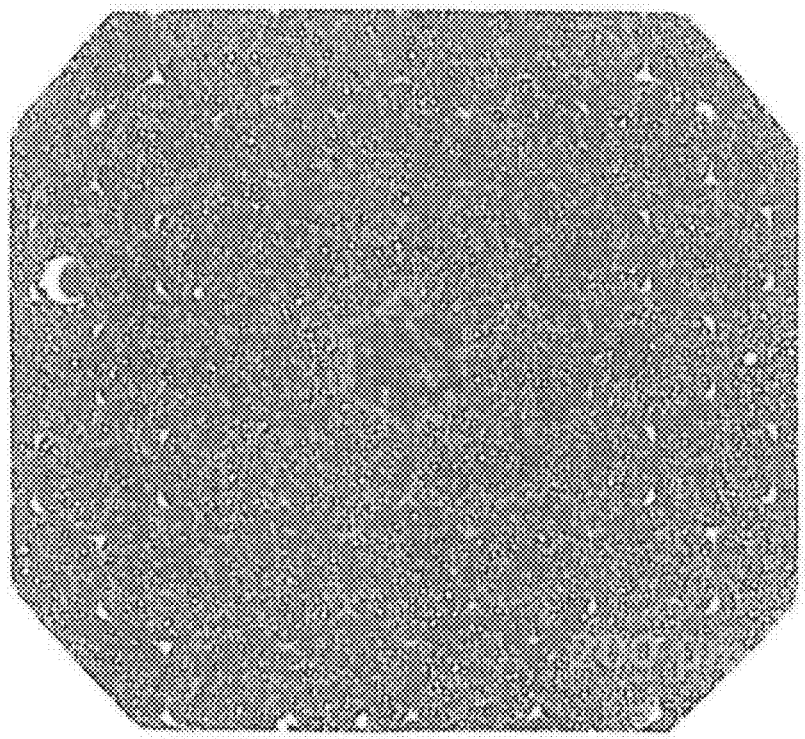
FIG. 7 shows an example of the observation unit 30 which employs a Nunc live cell array and provides several cells for each well.

FIG. 7 is a figure showing a state in which cells in a cell suspension liquid are provided (precipitated) in the observation unit 30 of the MWC system as with FIG. 6. As the observation unit 30, the Nunc live cell array is used. The cross sectional shape of each of wells we is a honeycomb shape, and the diameter (diameter of a circumscribed circle) of the wells we is 250 μm. In this figure, a view range is approximately 1500 μm (diameter), and six wells are arranged in each of the longitudinal and transverse directions. It turns out that hundred and several tens cells are provided for each of the wells we such that the cells do not overlap with each other.

Figure 8:
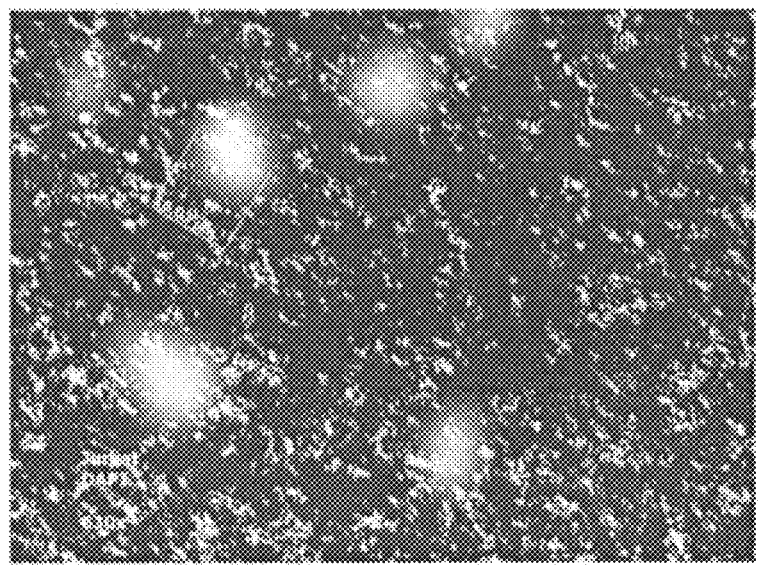
FIG. 8 shows an example of the observation unit 30 which employs a Nuclepore membrane as one of the through-hole filter systems.

FIG. 8 is a figure showing a state in which cells in a cell suspension liquid are provided in the observation unit 30 of the through-hole filter system. As the observation unit 30, the filter of a Nuclepore membrane is used. As a catalog value, the diameter of a through-hole is 0.4 μm or less. In FIG. 8, each of six light white round portions shows a cell, and a lead line (16.03 μm) in the shape of a character of ⊐ shows the diameter of one of the cells. As can be seen from FIG. 8, it turns out that cells are provided on the filter of the observation unit 30 such that the cells do not overlap with each other.

[Implementation Condition, Such as Cell Dyeing]

For the cells provided at Step S2, the immobilization and dyeing of cells are performed at Step S2-2 in the observation unit 30 (a Nunc live cell array or Nuclepore membrane). However, instead of this procedures, for the sediment at Step S1, the immobilization and dyeing (the following (1) to (6)) are performed at Step S1-2, thereafter, the sediment may be provided on the observation unit. Further, as a technique to facilitate the observation, natural dry adhesion may be conducted by still standing for two hours.

The respective equal amounts of a suspension liquid including Jurkat cells ($10^5$ to $10^6$ cells/ml) and a suspension liquid MCF-7 cells (about $10^2$ cells/ml) both of which are adjusted by culture are mixed, and 300 g of the resulting mixture liquid is subjected to centrifugal separation for five minutes, thereafter supernatant is discarded, and PBS (Phosphate-Buffered Saline, for example, invitrogen) is added to the sediment.

(1) Immobilization of Cells

The above-adjusted mixture liquid of Jurkat cells and MCF-7 cells is dropped on the observation unit 30, the liquid component is drained by utilization of capillarity or suction, and 3% PFA (paraformaldehyde, for example, manufactured by Wako Pure Chemical Industries) is added to the sediment to prepare a suspension liquid via still standing for 20 minutes.

(2) Washing and Removing of PFA

PBS is added, and drainage is achieved as with (1).

(3) Blocking

Blocking is performed by dropping of 3% BSA (for example, pierce)—PBS, still standings for 45 minutes, and then washing and removing by PBS.

(4) Primary Antibody Reaction

Anti-CK (mouse ConeA45-B/B3) and anti-CD45 (rabbit sc-25590) (anti-CK and anti-CD45 both, for example, AS diagnostik) are diluted by 100 times a stock solution and made to react by still standing for 45 minutes.

(5) Secondary Antibody Reaction

Alexa488-labeled anti-mouse IgG and Alexa555-labeled anti-rabbit IgG (both, for example, invitrogen) are diluted by 100 times a stock solution and made to react by still standing for 45 minutes.

(6) Dying of Nuclear

DAPI liquid (diluted by 400,000 times a stock solution, for example, invitrogen) is added, dying by still standing for 45 minutes.

(7) Enclosure

Cells are enclosed together with a fading inhibitor Pro-Long Gold (for example, invitrogea) by a cover glass.

(8) CTC Count

Cells each of which is indicated as a green fluorescence image via a 38HE filter (corresponding to Alexa488 (CK)) by a fluorescence microscope are counted.

EXPLANATION OF REFERENCE SIGNS

11 Light Source
12 Rotatable Polygon Minor
13 Motor
14 Scanning Optical System
21 Optical Guide
22 Light Receiving Section
23 Optical Filter
24 Photographing Section
25 Analyzing Section
30 Observation Unit
we Well
h Hole
40 Endless Belt

The invention claimed is:

1. A cell detecting method for detecting rare cells in a blood sample, comprising:
    a first step of performing pretreatment to remove red blood cells from a blood sample so as to obtain a cell suspension liquid containing leukocyte cells and rare cells;
    a second step of providing the cells contained in the cell suspension liquid obtained at the first step onto an observation region provided with a plurality of holes;
    a third step of photographing optically the cells provided on the observation region; and
    a fourth step of detecting rare cells from an image acquired by the photographing in the third step,
    wherein the plurality of holes disposed on the observation region are formed by a filter having a plurality of through-holes which are disposed with a predetermined pore density and each of which has a diameter smaller than the maximum diameter of the cells contained in the cell suspension liquid, and in the second step, the cell suspension liquid is made to pass through the filter so that the cells contained in the cell suspension liquid are provided on the filter.

2. The cell detecting method described in claim 1, further comprising a step of immobilizing the cells on the observation region between the second step and the third step.

* * * * *